(12) United States Patent
Hwang et al.

(10) Patent No.: US 10,400,070 B2
(45) Date of Patent: Sep. 3, 2019

(54) SELF-HEALING POLYSILSESQUIOXANES AND HYBRID FILM USING THE SAME

(71) Applicant: KOREA INSTITUTE OF SCIENCE AND TECHNOLOGY, Seoul (KR)

(72) Inventors: Seung Sang Hwang, Seoul (KR); Soon Man Hong, Seoul (KR); Chong Min Koo, Seoul (KR); Kyung Youl Baek, Seoul (KR); Albert Sung Soo Lee, Seoul (KR); Young Yeol Jo, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 2 days.

(21) Appl. No.: 15/833,400

(22) Filed: Dec. 6, 2017

(65) Prior Publication Data

US 2018/0155501 A1 Jun. 7, 2018

(30) Foreign Application Priority Data

Dec. 7, 2016 (KR) ........................ 10-2016-0165688

(51) Int. Cl.

| | | |
|---|---|---|
| *C08G 77/20* | (2006.01) | |
| *C08G 77/26* | (2006.01) | |
| *C08J 3/24* | (2006.01) | |
| *B01D 71/70* | (2006.01) | |
| *B01D 67/00* | (2006.01) | |
| *B01D 69/02* | (2006.01) | |
| *B01D 69/14* | (2006.01) | |
| *B01D 71/76* | (2006.01) | |
| *C09D 183/08* | (2006.01) | |
| *G01N 21/35* | (2014.01) | |
| *G01R 33/46* | (2006.01) | |
| *B01D 53/22* | (2006.01) | |
| *B01D 71/02* | (2006.01) | |

(52) U.S. Cl.
CPC ......... *C08G 77/26* (2013.01); *B01D 67/0093* (2013.01); *B01D 69/02* (2013.01); *B01D 69/148* (2013.01); *B01D 71/70* (2013.01); *B01D 71/76* (2013.01); *C08J 3/24* (2013.01); *C09D 183/08* (2013.01); *B01D 53/228* (2013.01); *B01D 71/027* (2013.01); *B01D 2323/30* (2013.01); *B01D 2325/24* (2013.01); *B01D 2325/44* (2013.01); *C08J 2383/08* (2013.01); *C08L 2203/16* (2013.01); *G01N 2021/3595* (2013.01); *G01R 33/46* (2013.01)

(58) Field of Classification Search
CPC ......... C08G 77/20; C08G 77/26; C08G 77/16
See application file for complete search history.

(56) References Cited

U.S. PATENT DOCUMENTS

| | | | | |
|---|---|---|---|---|
| 5,236,984 | A * | 8/1993 | Yamamoto | C09D 183/04 524/233 |
| 6,087,250 | A * | 7/2000 | Hyakutake | H01L 21/76801 257/E21.245 |
| 6,783,709 | B2 * | 8/2004 | Harreld | C08G 77/452 264/36.1 |
| 2004/0007792 | A1 * | 1/2004 | Harreld | C08G 77/452 264/36.1 |
| 2009/0156754 | A1 * | 6/2009 | Liu | C08F 290/148 525/431 |
| 2015/0340299 | A1 * | 11/2015 | Nakagawa | C08G 77/50 257/791 |
| 2016/0083526 | A1 * | 3/2016 | Hwang | C08G 77/442 522/78 |
| 2016/0107127 | A1 * | 4/2016 | Lee | B01D 69/125 96/4 |
| 2016/0200939 | A1 * | 7/2016 | Cho | C09D 183/04 136/257 |
| 2017/0120200 | A1 * | 5/2017 | Lee | B01D 53/228 |
| 2018/0037720 | A1 * | 2/2018 | Sugioka | C09K 3/1006 |

FOREIGN PATENT DOCUMENTS

| | | | |
|---|---|---|---|
| KR | 10-0932765 B1 | | 12/2009 |
| KR | 2016/046651 | * | 4/2016 |
| KR | 10-2016-0085604 A | | 7/2016 |
| KR | 2016/085604 | * | 7/2016 |
| WO | 2016/132889 | * | 8/2016 |

* cited by examiner

*Primary Examiner* — Margaret G Moore
(74) *Attorney, Agent, or Firm* — Rabin & Berdo, P.C.

(57) ABSTRACT

Disclosed is a self-healing polysilsesquioxane and a hybrid film using the same. Once crosslinked, the polysilsesquioxane copolymer can self-heal within several minutes at 100-120° C. The self-healing polysilsesquioxane copolymer can be prepared into a hybrid material in the form of a film. Because the hybrid film has an excellent ability of self-healing the damage caused by external impact, it is applicable to wide applications such as gas separation membranes, etc., without limitation.

14 Claims, 21 Drawing Sheets

SELF-HEALING POLYSILSESQUIOXANES AND HYBRID FILM USING THE SAME

CROSS-REFERENCE TO RELATED APPLICATIONS

This application claims, under 35 U.S.C. § 119, the priority of Korean Patent Application No. 10-2016-0165688 filed on Dec. 7, 2016 in the Korean Intellectual Property Office, the disclosure of which is incorporated herein by reference in its entirety.

TECHNICAL FIELD

The present disclosure relates to a self-healing polysilsesquioxane and a hybrid film using the same.

BACKGROUND

Crosslinked polymer materials have been studied and used in various applications due to superior mechanical properties, thermal stability, solvent resistance, etc. However, because the crosslinked polymer materials are sensitive to unexpected mechanical damage caused by continued force and external impact, they have limited life span in recycling.

In order to solve this problem, the development of self-healing polymer materials is drawing attentions as a new technology. Self-healing polymers can be largely classified into 1) extrinsic self-healing polymers and 2) intrinsic self-healing polymers. The extrinsic self-healing polymers self-heal by a healing additive injected directly thereinto, whereas the intrinsic self-healing polymers self-heal through chemical bonding.

In particular, regarding the preparation of intrinsic self-healing polymers, the Diels-Alder reaction whereby cross-linkages are formed reversibly depending on temperature. Many self-healing polymer materials have been proposed through theses and patents and self-healing polymers using the organic-inorganic hybrid material polysilsesquioxane have also been studied a lot.

However, the existing self-healing polymer materials require a process of blending dienes and dienophiles for the Diels-Alder reaction, which renders problems in compatibility and uniformity on a nanoscale level. In addition, they have the problems of nonuniform film surface, low transparency, imperfect crosslinkage and inability of recycling.

REFERENCES OF THE RELATED ART

Patent Document

Korean Patent Registration No. 10-0932765.

SUMMARY

In order to solve the problems described above, the present disclosure is directed to preparing a self-healing polysilsesquioxane copolymer and providing a hybrid film that can be used in various applications such as a gas separation membrane, etc. using the copolymer.

In an aspect, the present disclosure relates to a self-healing polysilsesquioxane copolymer represented by Chemical Formula 1:

[Chemical Formula 1]

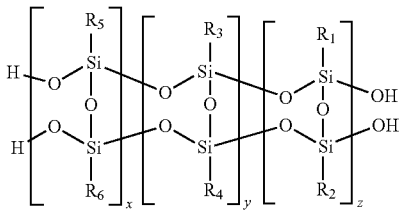

wherein
each of $R_1$ through $R_6$, which are different from each other, is independently hydrogen or $-R_7-R_8$,
$R_7$ is a valence bond or $C_1$-$C_6$ alkyl,
$R_8$ is selected from a group consisting of a valence bond, $C_1$-$C_6$ alkyl, $-OR_9$, an organic functional group containing a diene and an organic material containing a dienophile,
$R_9$ is selected from a group consisting of a hydrogen, $C_1$-$C_5$ alkyl, acryl, epoxy and epoxycyclohexyl,
x is an integer from 1 to 10,000,
y is an integer from 1 to 10,000, and
z is an integer from 1 to 10,000.

In another aspect, the present disclosure relates to hybrid film containing the polysilsesquioxane copolymer.

In another aspect, the present disclosure relates to a gas separation membrane containing the polysilsesquioxane copolymer.

According to the present disclosure, a polysilsesquioxane copolymer which can self-heal within several minutes at 100-120° C. after being crosslinked at 80-100° C. can be provided. The polysilsesquioxane copolymer, having a diene and a dienophile introduced together in the copolymer, can be used as a single material.

In addition, because the self-healing polysilsesquioxane copolymer significantly improves physical properties such as heat resistance, mechanical strength, light transmittance, solubility and processability when applied to a hybrid material such as a film, it is widely applicable as a coating material for displays or automobiles, in addition to gas separation membranes.

BRIEF DESCRIPTION OF DRAWINGS

FIGS. 10A and 10B show physical properties before scratch, and FIGS. 10C and 10D show physical properties after scratch.

FIG. 11A: Example 12, FIG. 11B: Example 13, FIG. 11C: Example 14.

FIG. 12A: Example 12, FIG. 12B: Example 13, FIG. 12C: Example 14.

DETAILED DESCRIPTION OF EMBODIMENTS

Figure 1:
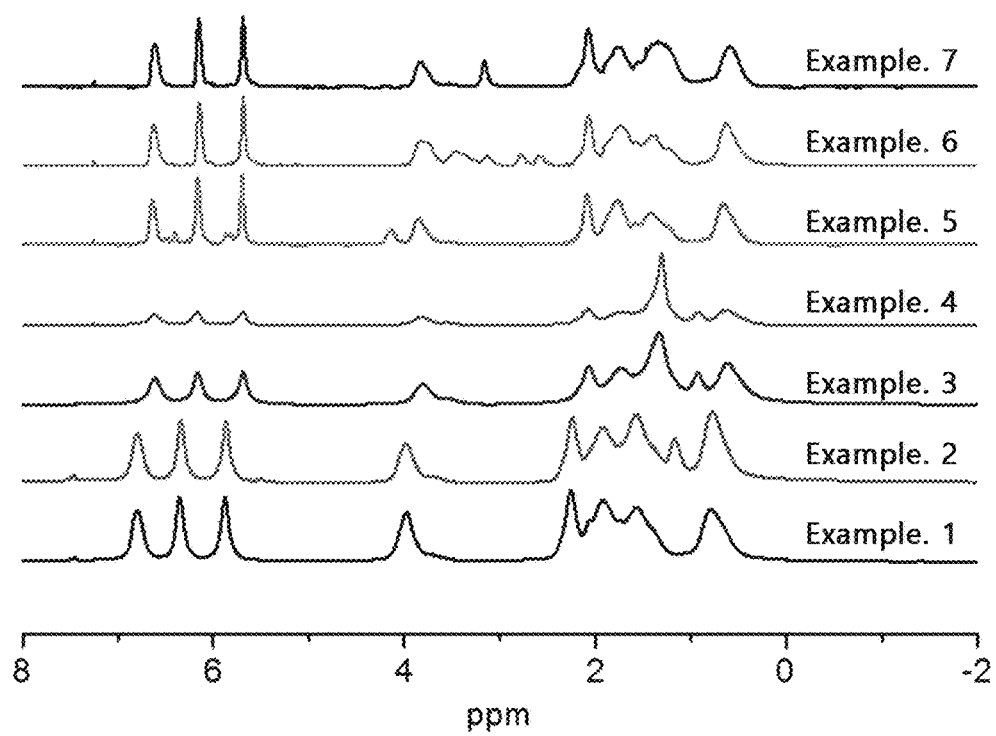
FIG. 1 shows a $^1$H NMR (nuclear magnetic resonance) analysis result of polysilsesquioxane copolymers of Examples 1-7.

Hereinafter, various aspects and exemplary embodiments of the present disclosure are described in more detail.

In an aspect, the present disclosure provides a self-healing polysilsesquioxane copolymer represented by Chemical Formula 1:

[Chemical Formula 1]

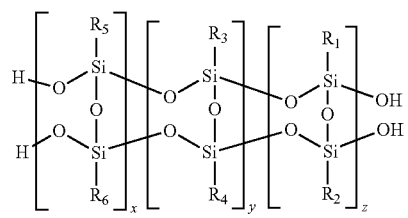

wherein
each of $R_1$ through $R_6$, which are different from each other, is independently hydrogen or —$R_7$—$R_8$,
$R_7$ is a valence bond or $C_1$-$C_6$ alkyl,
$R_8$ is selected from a group consisting of a valence bond, $C_1$-$C_6$ alkyl, —$OR_9$, an organic functional group containing a diene and an organic material containing a dienophile,
$R_9$ is selected from a group consisting of a hydrogen, $C_1$-$C_5$ alkyl, acryl, epoxy and epoxycyclohexyl,
x is an integer from 1 to 10,000,
y is an integer from 1 to 10,000, and
z is an integer from 1 to 10,000.

More specifically, $R_1$ and $R_2$ are identical and an organic functional group containing a diene, $R_3$ and $R_4$ identical and an organic material containing a dienophile, and $R_5$ and $R_6$ are —$R_7$—$R_8$. Further more specifically, $R_7$ is $C_1$-$C_6$ alkyl and $R_8$ is $C_1$-$C_6$ alkyl or —$OR_9$, wherein $R_9$ is acryl, epoxy or epoxycyclohexyl.

A Diels-Alder reaction occurs between the organic functional group containing a diene and the organic material containing a dienophile when heat is applied to the polysilsesquioxane copolymer. The Diels-Alder reaction occurs according to Scheme 1. As a result, the polysilsesquioxane copolymer has thermal reversibility.

[Scheme 1]

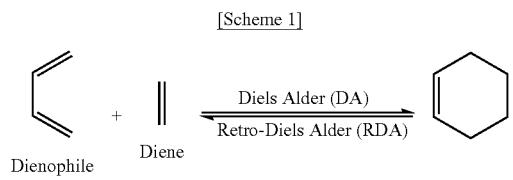

That is to say, the polysilsesquioxane copolymer forms a crosslinked copolymer within a predetermined temperature range through the Diels-Alder reaction between the organic functional group containing a diene and the organic material containing a dienophile. Crosslinkages may be formed via the Diels-Alder reaction between the organic functional group containing a diene and the organic material containing a dienophile and destroyed via the reverse reaction known as the retro-Diels-Alder reaction.

Specifically, the organic functional group containing a diene may be represented by Chemical Formula 2 and the organic material containing a dienophile may be represented by Chemical Formula 3:

[Chemical Formula 2]

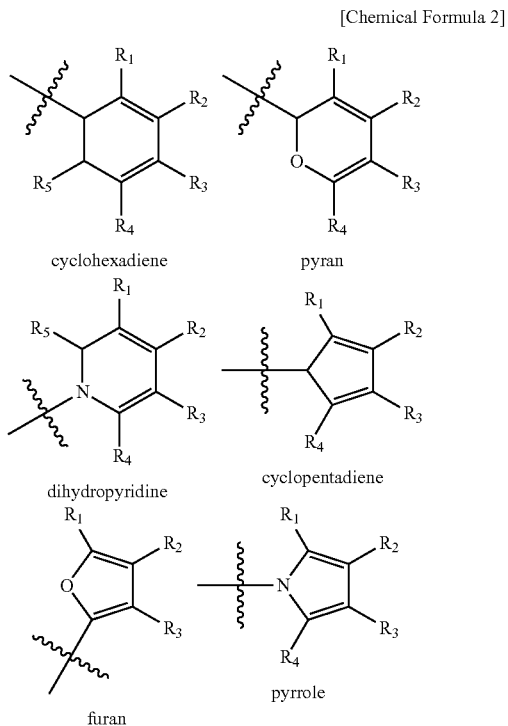

[Chemical Formula 3]

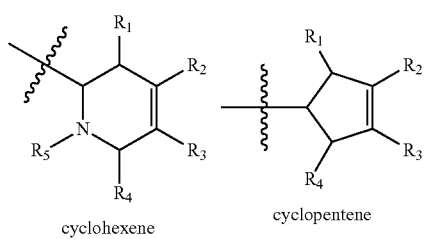

wherein each of $R_1$ through $R_5$, which are different from each other, is independently hydrogen, substituted or unsubstituted branched $C_1$-$C_{30}$ alkyl or $C_3$-$C_{10}$ cycloalkyl, wherein the substitution is with an amine or hydroxyl functional group. In Chemical Formulas 2 and 3, at least one of $R_1$ through $R_5$ may be substituted with a trialkoxysilane group to be used as a polymerization monomer of a silsesquioxane.

More specifically, in Chemical Formula 2-3, each of $R_1$ through $R_5$, which are different from each other, may be independently hydrogen or $C_1$-$C_5$ alkyl. In this case, the self-healing is achieved quickly within several minutes. When $R_1$ through $R_5$ are other functional groups, the self-healing is achieved very slowly within several hours.

Specifically, the polysilsesquioxane copolymer may have a number-average molecular weight ($M_n$) of 100-100,000. Outside this range, the copolymer exhibits physical properties which are difficult for film formation.

In particular, the polysilsesquioxane copolymer may be a ladder-type polysilsesquioxane (LPSQ). Because this structure is structurally stable and exhibits high thermal stability and good compatibility with an organic solvent, it is useful as an organic-inorganic hybrid material.

If the polysilsesquioxane copolymer is a polyoctahedral polyhedral silsesquioxane (POSS), it is difficult to be prepared into a film because it has a small molecular weight and is crystalline. In addition, it is difficult to be applied industrially due to unsatisfactory physical properties.

More specifically, the polysilsesquioxane copolymer may have a structure of one of Chemical Formulas 1a to 1g.

[Chemical Formula 1a]

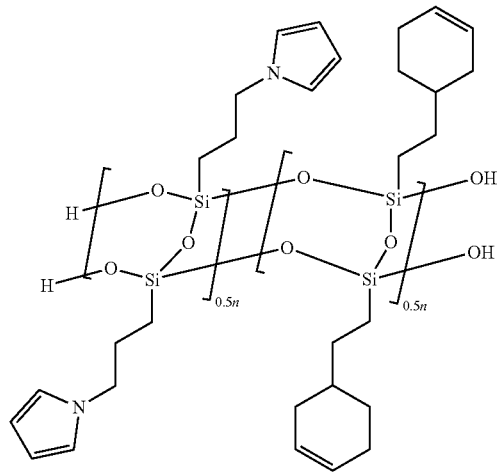

[Chemical Formula 1b]

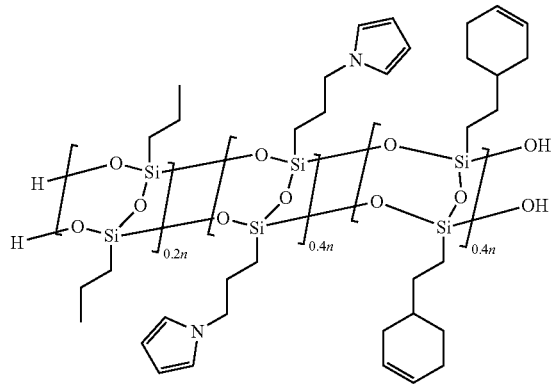

[Chemical Formula 1c]

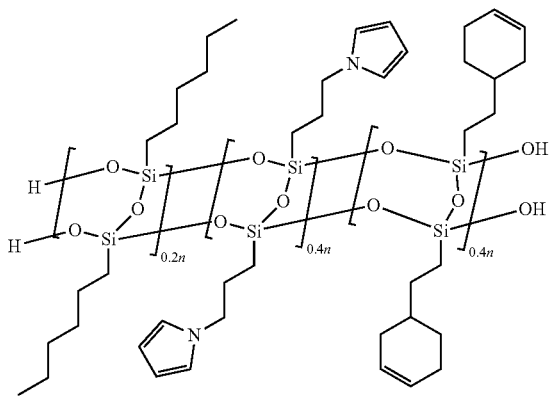

[Chemical Formula 1d]

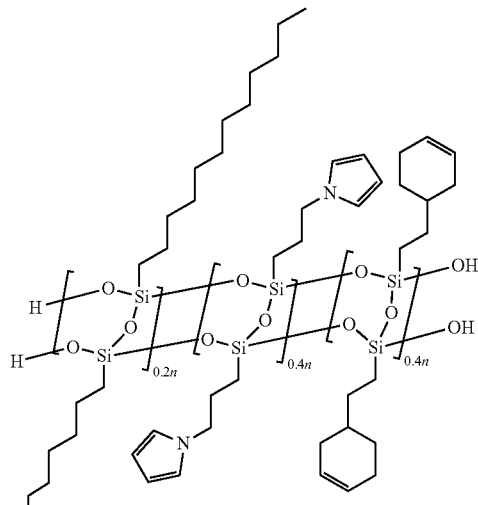

[Chemical Formula 1e]

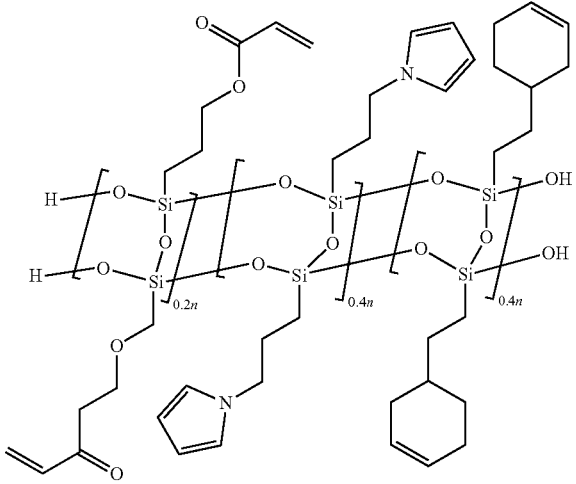

[Chemical Formula 1f]

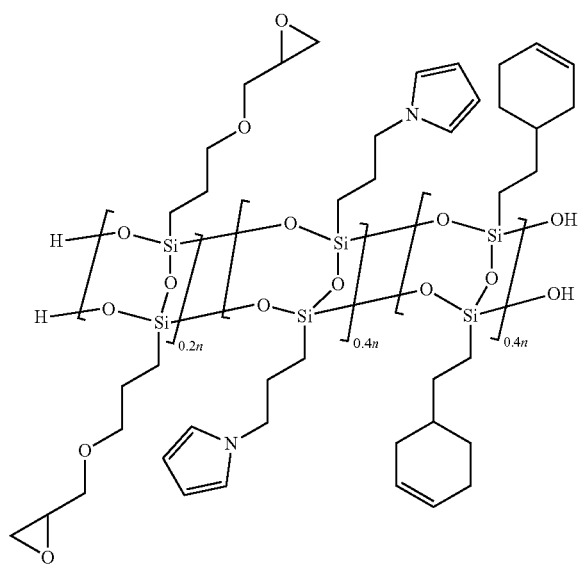

[Chemical Formula 1g]

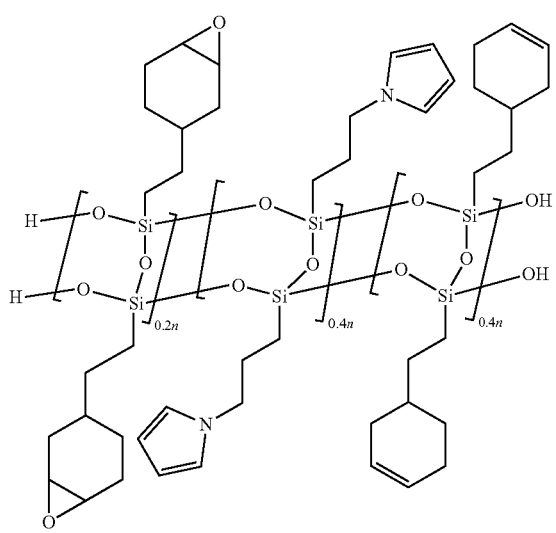

Once being crosslinked at 80-100° C., the ladder-type polysilsesquioxane copolymer self-heals at 100-120° C. within several minutes, as demonstrated in the examples described later and FIGS. 9 and 10.

In an exemplary embodiment, the ladder-type polysilsesquioxane copolymer may be prepared by reacting a trialkoxysilane monomer, an organic material containing a diene and an organic material containing a dienophile at 20-30° C. for 50-150 hours and then purifying the product, as shown in Scheme 2.

[Scheme 2]

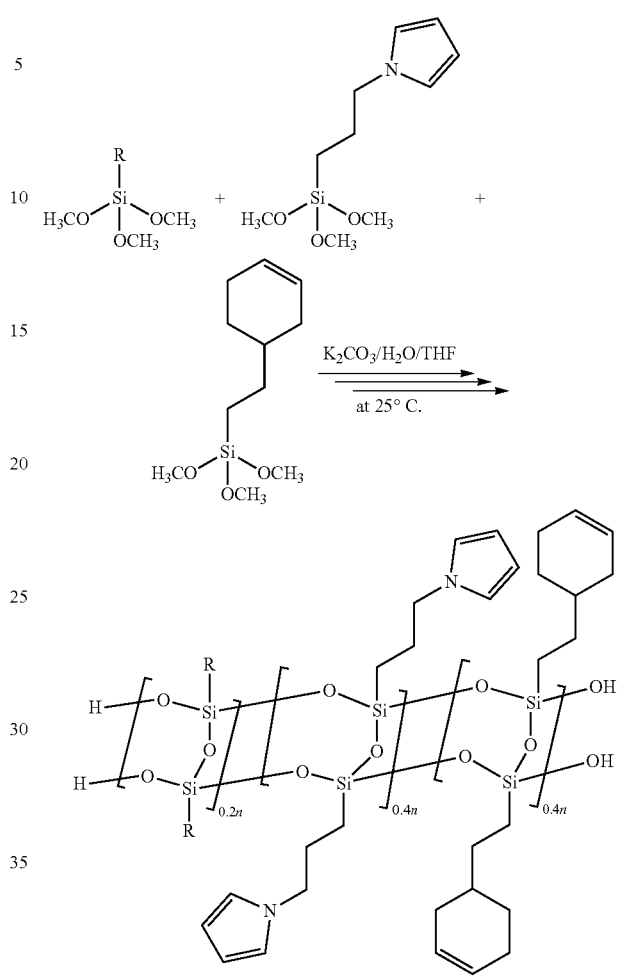

In another exemplary embodiment, a non-ladder-type polysilsesquioxane copolymer may be synthesized selectively by preparing a water-containing organic solution containing a trialkoxysilane monomer, an organic solvent, water and a catalyst and then controlling the amount of the organic solvent or water in the water-containing organic solution, although not being limited thereto.

In another aspect, the present disclosure relates to a hybrid film containing the polysilsesquioxane copolymer. Specifically, the hybrid film (thickness: 1 nm to 500 μm) may have a light transmittance of 80-100% at a wavelength of 500-800 nm. Therefore, the hybrid material is widely applicable as a coating material for displays or automobiles.

In addition, the hybrid film containing the polysilsesquioxane copolymer containing a photocurable organic functional group may be prepared into a high-strength thermosetting hybrid film through a primary photocuring process.

In another aspect, the present disclosure relates to a gas separation membrane containing the polysilsesquioxane copolymer.

Hereinafter, the present disclosure will be described in more detail through examples. However, the scope of the present disclosure is not reduced or limited by the following examples. It will be obvious that those of ordinary skill in the art can easily carry out the present disclosure for which experimental results are not specifically described on the basis of the disclosure of the present disclosure including the examples and that such modifications and changes belong to the scope of the present disclosure.

The experimental results presented below are only representative experimental results of the examples and comparative examples.

Example 1

Synthesis of Ladder-Type Polysilsesquioxane (LPCSQ55)

a) 0.01 g of potassium carbonate as a catalyst previously dissolved in 1.2 g of distilled water was stirred with 2 g of tetrahydrofuran for 20 minutes.

b) 0.04 mol of N-(3-trimethoxysilylpropyl)pyrrole (ABCR, 95%) as an organic material containing a diene and 0.04 mol of ethyltrimethoxysilane (ABCR, 97%) as an organic material containing a dienophile were added dropwise to the solution of a) with stirring. Upon completion of the addition, the mixture was reacted at 25° C. for 96 hours. After purification by fractional distillation using a water-immiscible solvent that can dissolve polysilsesquioxane-based materials, such as chloroform, methylene chloride, toluene, xylene, etc., a ladder-type polysilsesquioxane represented by Chemical Formula 1a was synthesized ($M_w$=13,000 (based on polystyrene), yield=95%).

[Chemical Formula 1a]

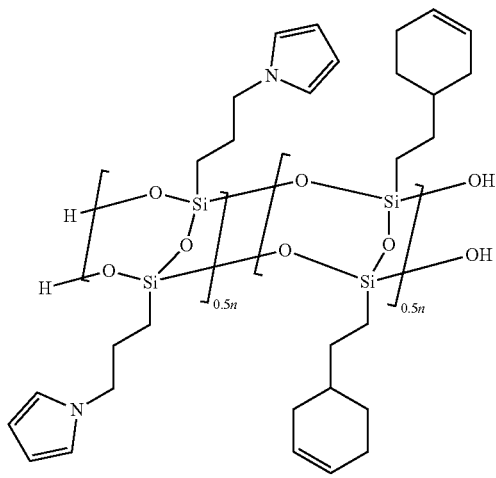

Example 2

Synthesis of Ladder-Type Polysilsesquioxane (LPrPCSQ244)

a) The same procedure as in Example 1 was conducted.

b) 0.016 mol of propyltrimethoxysilane, 0.032 mol of N-(3-trimethoxysilylpropyl)pyrrole and 0.032 mol of 2-(3-cyclohexenyl)ethyltrimethoxysilane were added dropwise to the solution of a) with stirring. Upon completion of the addition, the mixture was reacted at 25° C. for 96 hours. After purification by fractional distillation using a water-immiscible solvent that can dissolve polysilsesquioxane-based materials, such as chloroform, methylene chloride, toluene, xylene, etc., a ladder-type polysilsesquioxane represented by Chemical Formula 1b was synthesized ($M_w$=23,000 (based on polystyrene), yield=95%).

[Chemical Formula 1b]

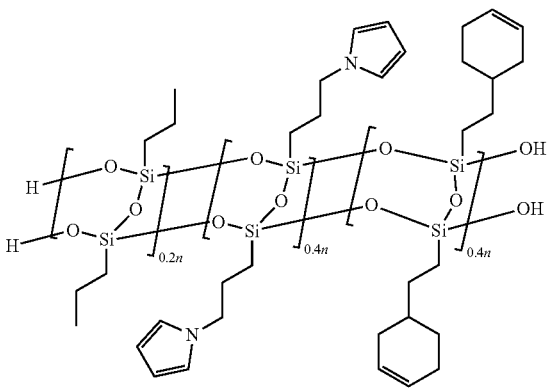

Example 3

Synthesis of Ladder-Type Polysilsesquioxane (LHPCSQ244)

A ladder-type polysilsesquioxane represented by Chemical Formula 1c was synthesized in the same manner as in Example 2, except that hexyltrimethoxysilane was used instead of the propyltrimethoxysilane ($M_w$=11,000 (based on polystyrene), yield=95%).

[Chemical Formula 1c]

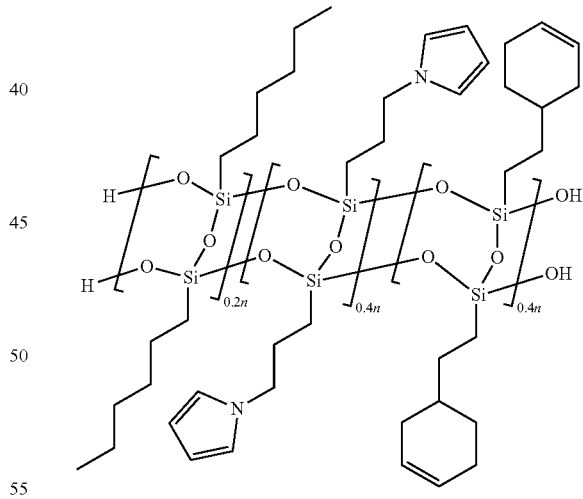

Example 4

Synthesis of Ladder-Type Polysilsesquioxane (LDPCSQ244)

A ladder-type polysilsesquioxane represented by Chemical Formula 1d was synthesized in the same manner as in Example 2, except that dodecyltrimethoxysilane was used instead of the propyltrimethoxysilane ($M_w$=11,000 (based on polystyrene), yield=95%).

[Chemical Formula 1d]

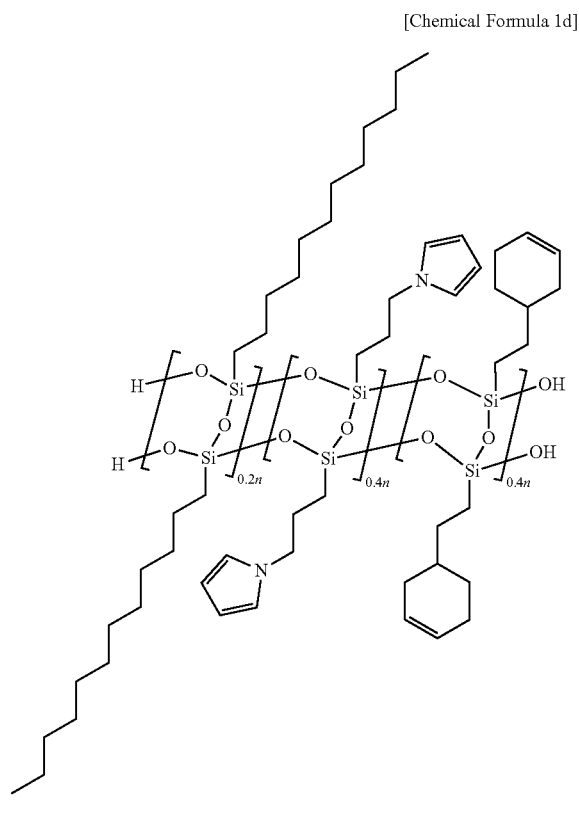

Example 5

Synthesis of Ladder-Type Polysilsesquioxane (LPAPCSQ244)

A ladder-type polysilsesquioxane represented by Chemical Formula 1e was synthesized in the same manner as in Example 2, except that 3-acryloxypropyltrimethoxysilane was used instead of the propyltrimethoxysilane ($M_w$=13,000 (based on polystyrene), yield=95%).

[Chemical Formula 1e]

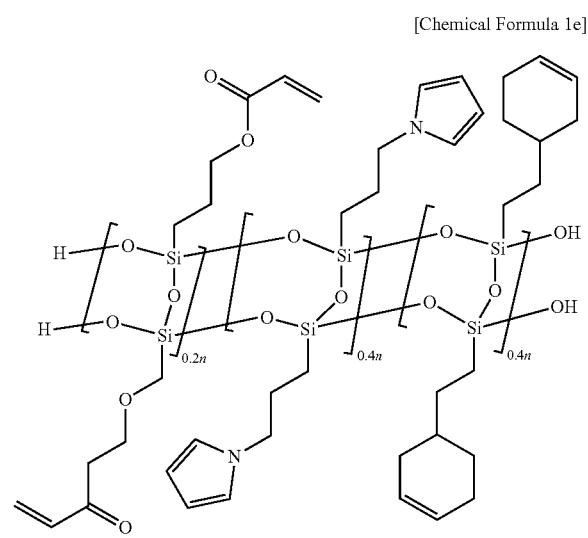

Example 6

Synthesis of Ladder-Type Polysilsesquioxane (LPGPCSQ244)

A ladder-type polysilsesquioxane represented by Chemical Formula 1f was synthesized in the same manner as in Example 2, except that 3-glycidoxypropyltrimethoxysilane was used instead of the propyltrimethoxysilane ($M_w$=12,000 (based on polystyrene), yield=95%).

[Chemical Formula 1f]

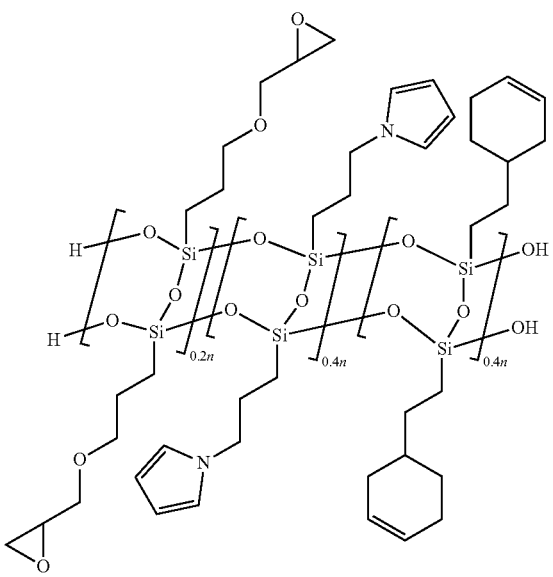

Example 7

Synthesis of Ladder-Type Polysilsesquioxane (LPCEPCSQ244)

A ladder-type polysilsesquioxane represented by Chemical Formula 1g was synthesized in the same manner as in Example 2, except that 2-3-cyclohexylepoxyethyltrimethoxysilane was used instead of the propyltrimethoxysilane ($M_w$=10,000 (based on polystyrene), yield=95%).

[Chemical Formula 1g]

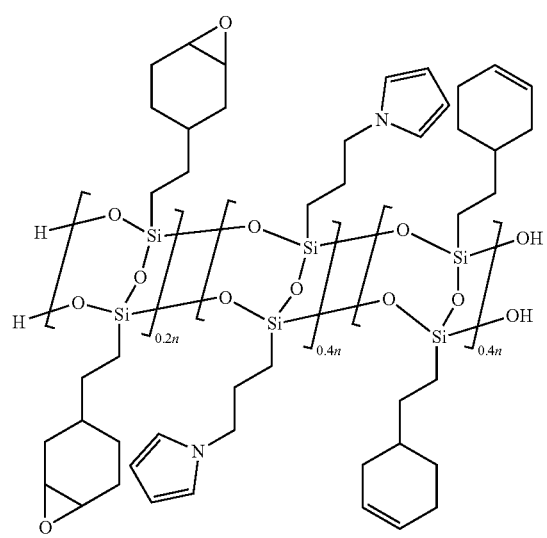

Examples 8-11

Preparation of Hybrid Film Using Ladder-Type Polysilsesquioxane

The polysilsesquioxane copolymers of Examples 1-4 were prepared into transparent solutions by dissolving in tetrahydrofuran to 50 wt %. The solution was drop-casted on a glass substrate. After drying at room temperature for a day and then drying in vacuo at 40° C. for 2 hours, a 50-μm-thick hybrid film was prepared.

Examples 12-14

Preparation of Photocurable/Thermally Self-Healing Hybrid Film (a) A transparent solution was prepared by dissolving each of the self-healing polysilsesquioxanes prepared in Examples 5-7 in tetrahydrofuran to 50 wt %. A transparent solution was prepared by adding 1 wt % 1-hydroxycyclohexyl phenyl ketone (Irgacure 184, BASF) as a photoinitiator to the solution of Example 5 (LPAPCSQ244) and 3 wt % (4-methylphenyl)[4-(2-methylpropyl)phenyl]iodonium hexafluorophosphate (Irgacure 250, BASF) as a photoinitiator to the solutions of Example 6 (LPGPCSQ244) and Example 7 (LPCEPCSQ244).

(b) The solution was drop-casted on a glass substrate. After drying at room temperature for a day and then drying in vacuo at 40° C. for 2 hours, a 50-μm-thick hybrid film was prepared. Then, a photocurable/thermally self-healing hybrid film was prepared by irradiating UV at 500 mJ/cm².

Test Example 1: NMR, FT-IR and XRD Analyses $^1$H NMR, $^{29}$Si NMR and FT-IR analyses were conducted for the ladder-type polysilsesquioxane copolymers of Examples 1-7. The result is shown in FIGS. 1-3 and 8.

Figure 2:
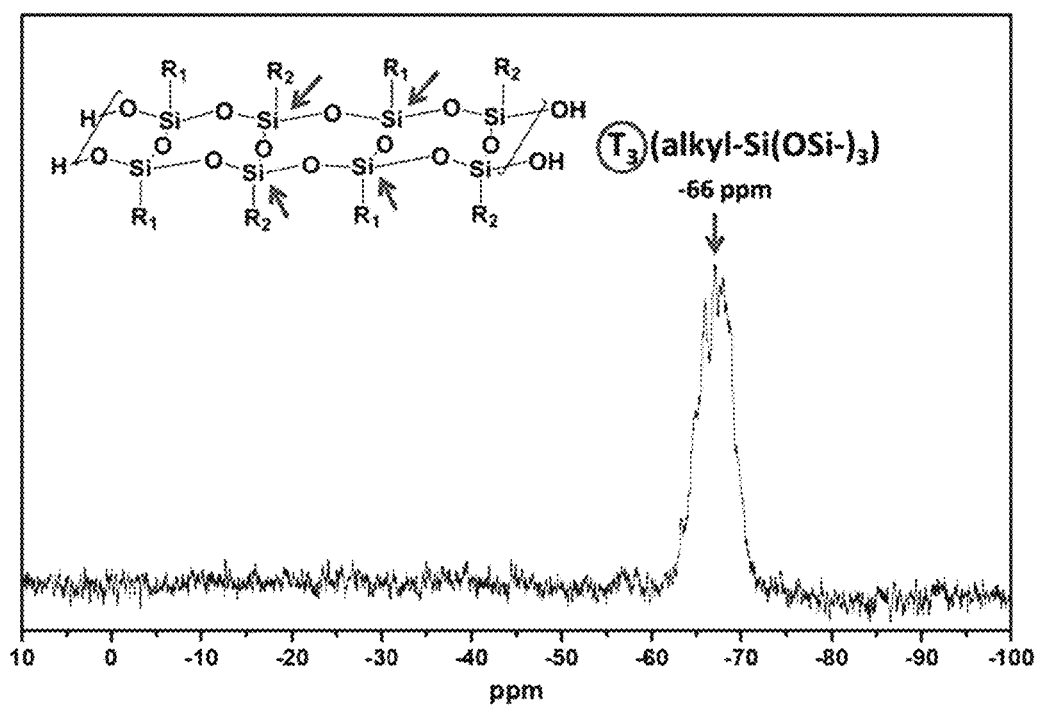
FIG. 2 shows a $^{29}$Si NMR (nuclear magnetic resonance) analysis result of a polysilsesquioxane copolymer of Example 1.
Figure 3:
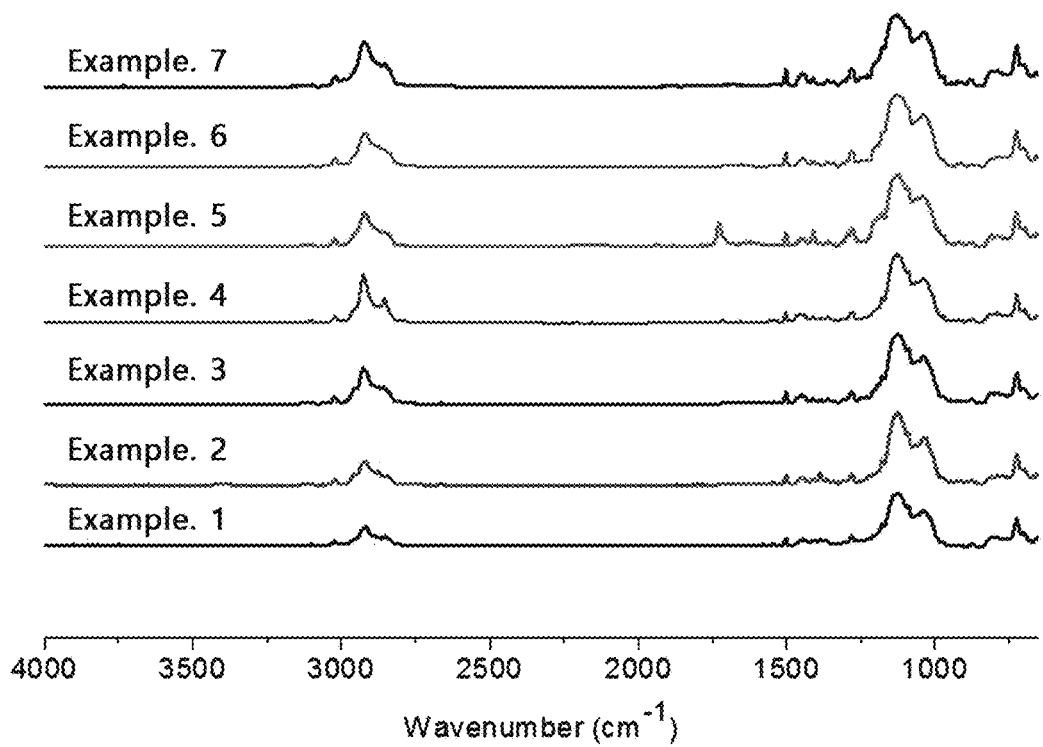
FIG. 3 shows a FT-IR (Fourier-transform infrared spectroscopy) analysis result of polysilsesquioxane copolymers of Examples 1-7.
Figure 8:
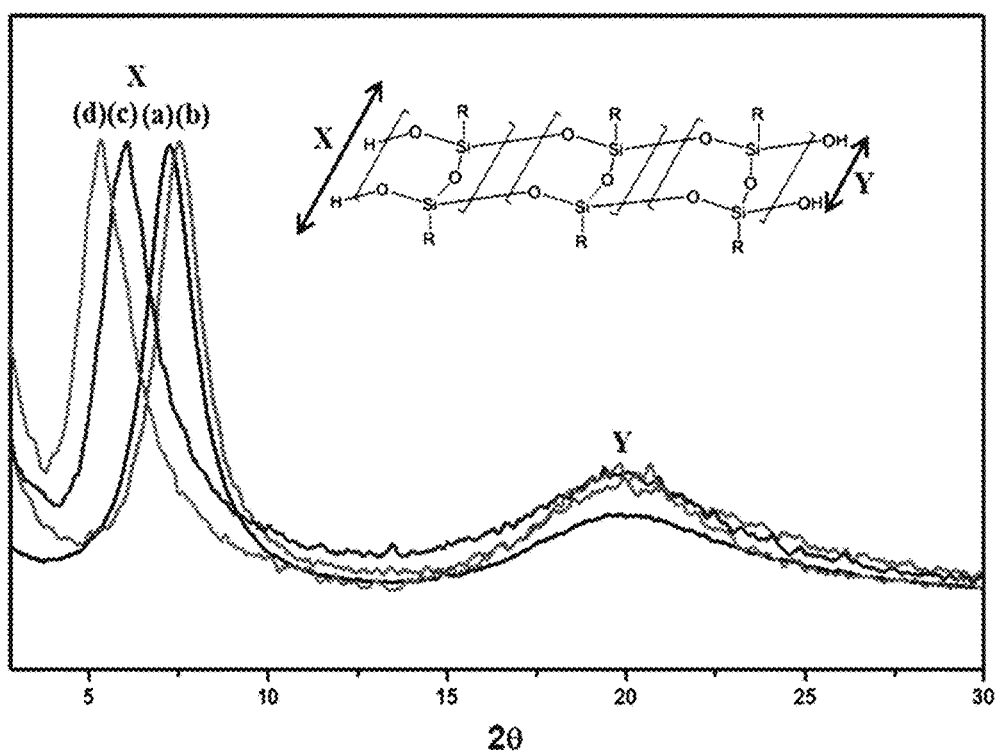
FIG. 8 shows an XRD analysis result of a polysilsesquioxane copolymer of Example 1.

FIG. 1 shows the $^1$H NMR analysis result, FIG. 2 shows the $^{29}$Si NMR analysis result, FIG. 3 shows the FT-IR analysis result and FIG. 8 shows the XRD analysis result.

FIG. 1 confirms the structure of the polysilsesquioxane copolymers. Peaks indicated by a-g can be identified. From FIG. 2, the alkyl-Si(OSi—)$_3$ peak representing the ladder-type structure can be identified.

FIG. 3 shows the typical Si—O—Si bond, n-pyrrole and cyclohexenyl peaks of the ladder-type silsesquioxane of Examples 1-7. FIG. 8 shows the XRD analysis result showing inter- and intra-polymer spacings. It can be seen that the inter-polymer spacing of the ladder-type silsesquioxane increases with the length of the propyl, hexyl and dodecyl groups of LPrPCSQ244, LHPCSQ244 and LDPCSQ244.

Test Example 2: TGA and DSC Analyses

The hybrid films of Examples 8-11 were analyzed by TGA and DSC. The result is shown in FIGS. 4 and 5.

Figure 4:
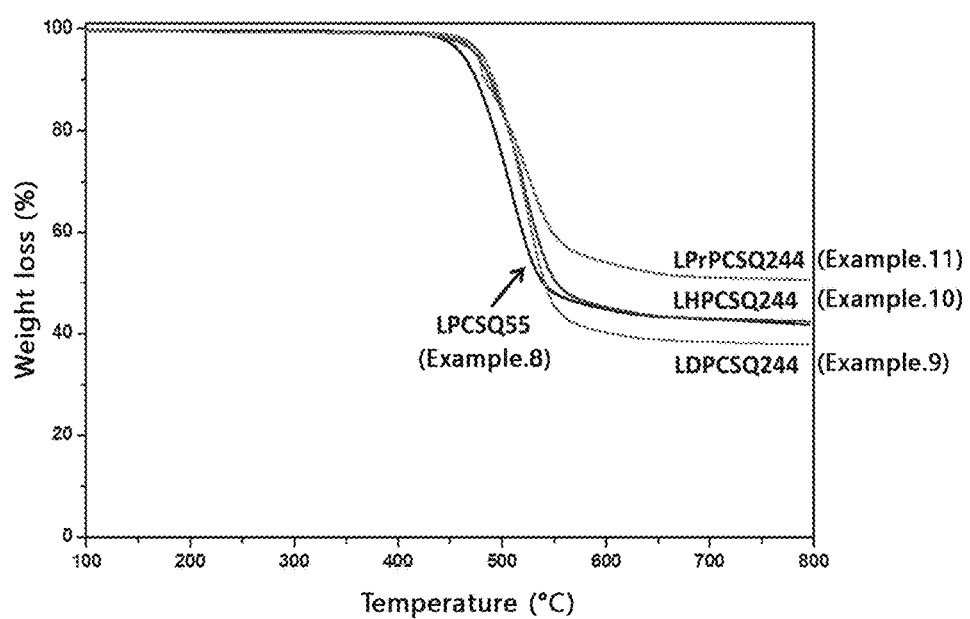
FIG. 4 shows a TGA (thermogravimetric analysis) result of hybrid films of Examples 8-11.

FIG. 4 shows the TGA analysis result. It can be seen that weight loss was 70-80% at 500° C. or higher and was maintained at about 40% or more as high as 800° C.

Figure 5:
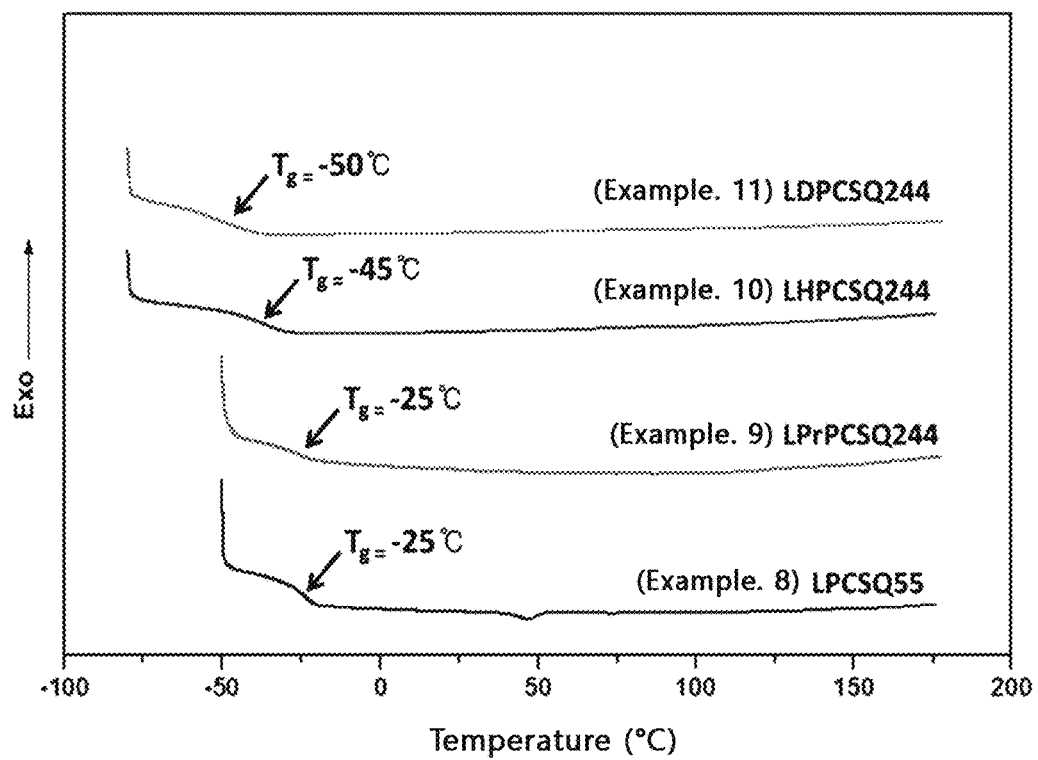
FIG. 5 shows a DSC (differential scanning calorimetry) analysis result of hybrid films of Examples 8-11.

From the DSC analysis result of FIG. 5, it was confirmed that $T_g$ is maintained at −50 to −25° C.

Test Example 3: Transparency Analysis

The transparency of the hybrid films of Examples 8-11 was analyzed by UV-vis (ultraviolet-visible) spectroscopy. The result is shown in FIG. 6.

Figure 6:
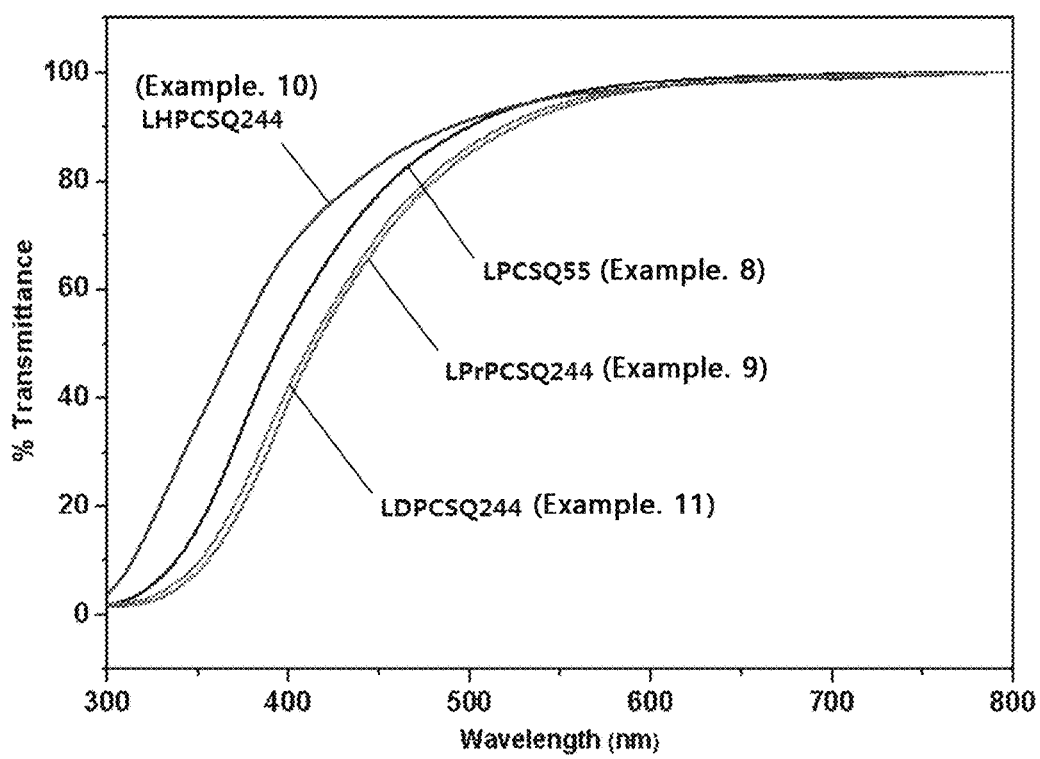
FIG. 6 shows the transparency of hybrid films of Examples 8-11 analyzed by UV-Vis (ultraviolet-visible) spectroscopy.

Referring to FIG. 6, it can be seen that the light transmittance was about 80-100% at 500-800 nm.

Test Example 4: Analysis of Self-Healing Ability Through Scratch Test

Figure 7:
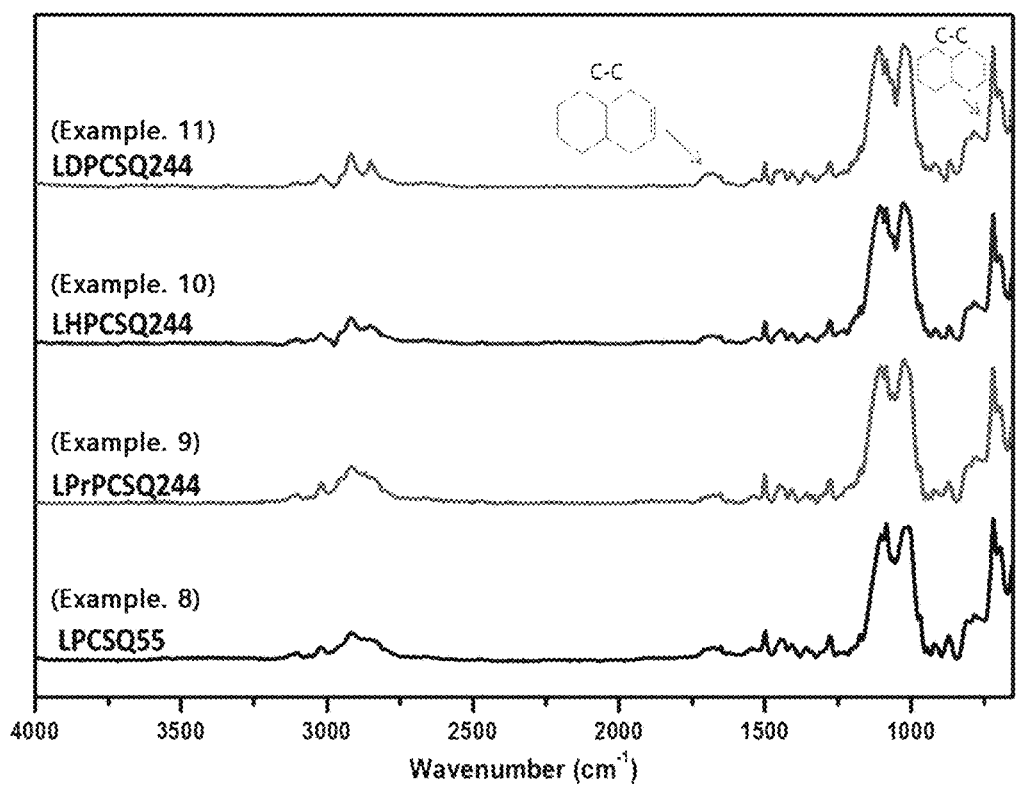
FIG. 7 shows an FT-IR analysis result of hybrid films of Examples 8-11 after thermal curing.

In order to investigate the self-healing ability of the hybrid films of Examples 8-11, each hybrid film was cured at 90° C. for 2 hours via the Diels-Alder reaction and then a scratch with a size of ~100 μm was made. Then, the occurrence of self-healing was analyzed under an optical microscope. The result is shown in FIGS. 9 and 10. Also, the cured hybrid film was analyzed by FT-IR. The result is shown in FIG. 7.

Figure 9:
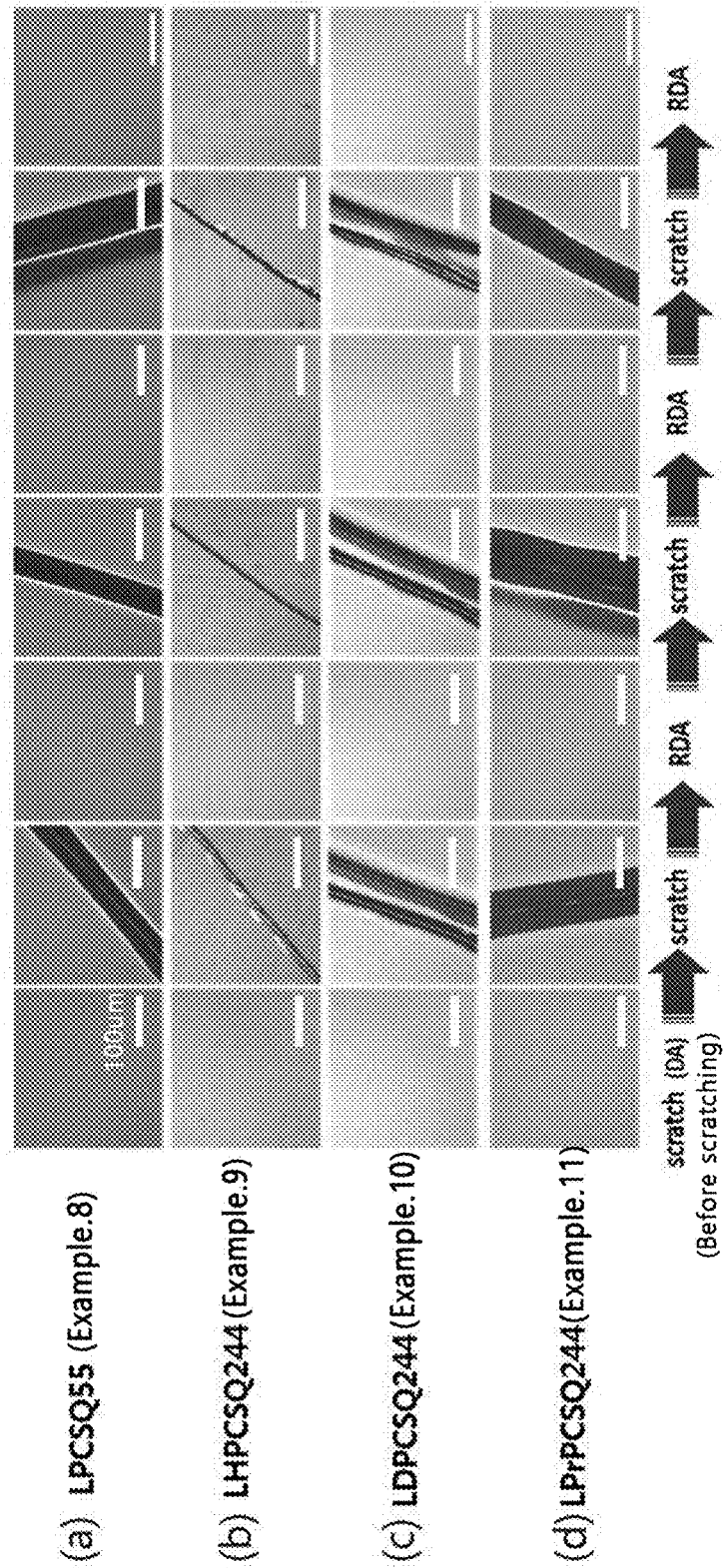
FIG. 9 shows a scratch test result of hybrid films of Examples 8-11 before and after thermally reversible self-healing.
Figure 10A:
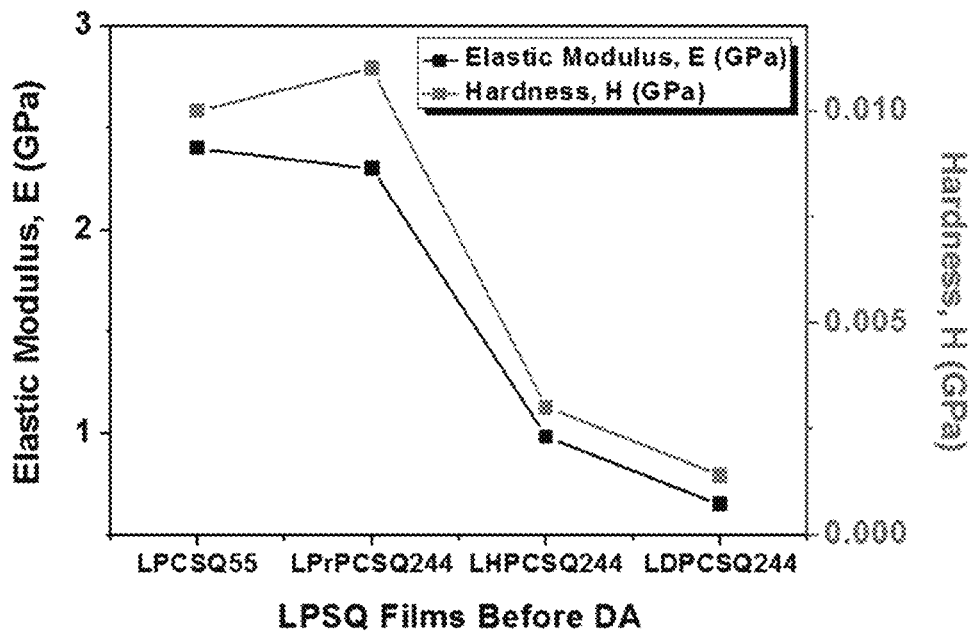
FIGS. 10A to 10D shows a nanoindentation analysis result of hybrid films of Examples 1-4 before and after thermally reversible self-healing.
Figure 10B:
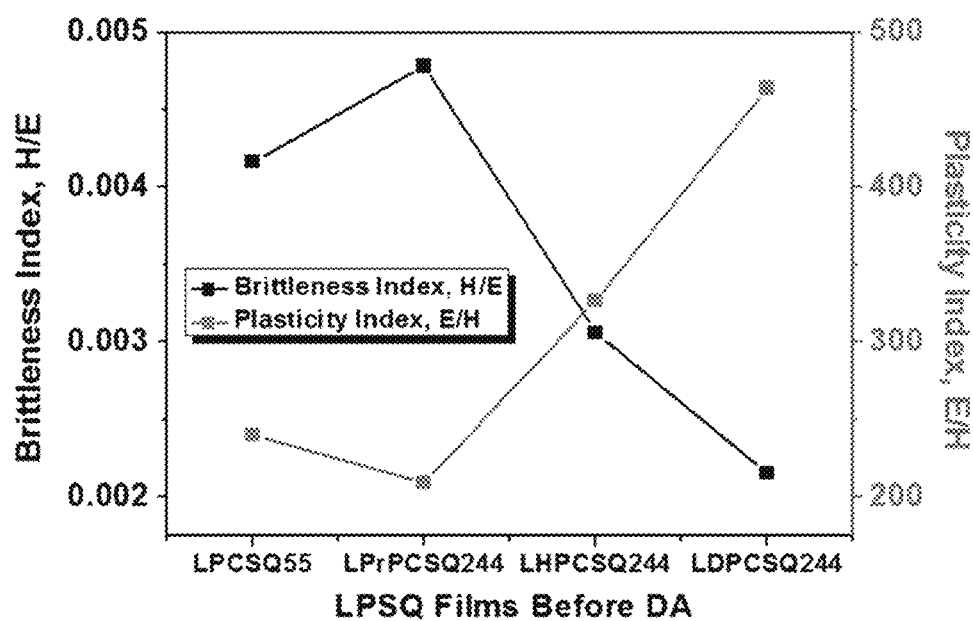
Figure 10C:
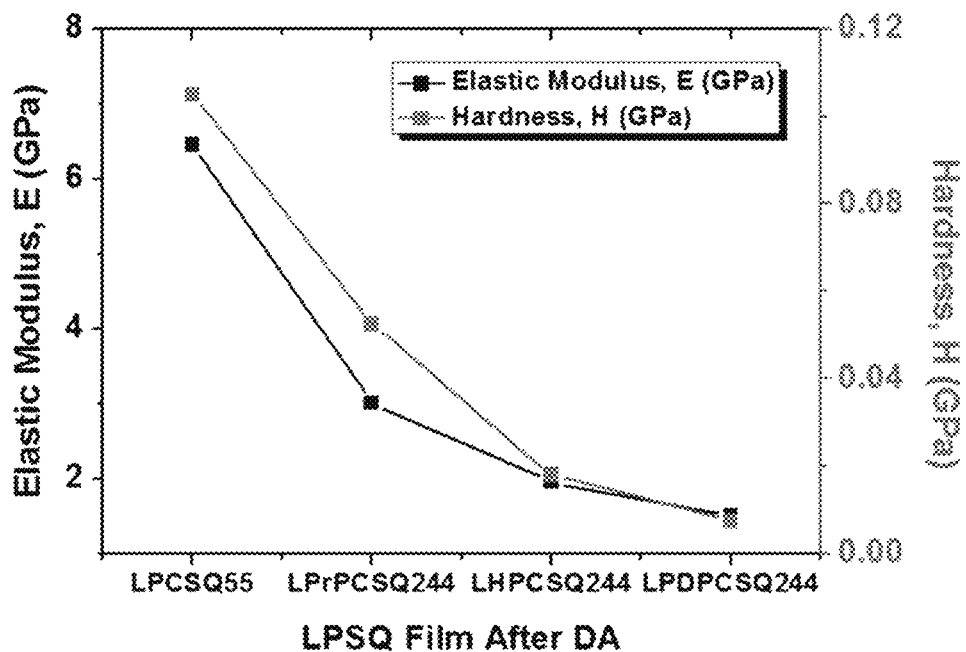
Figure 10D:
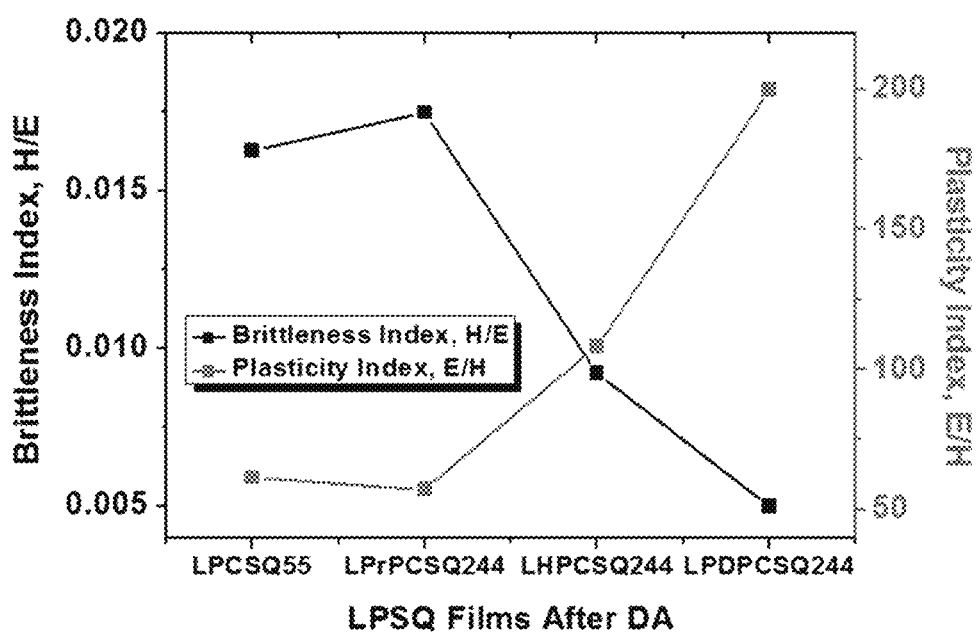
Figure 11A:
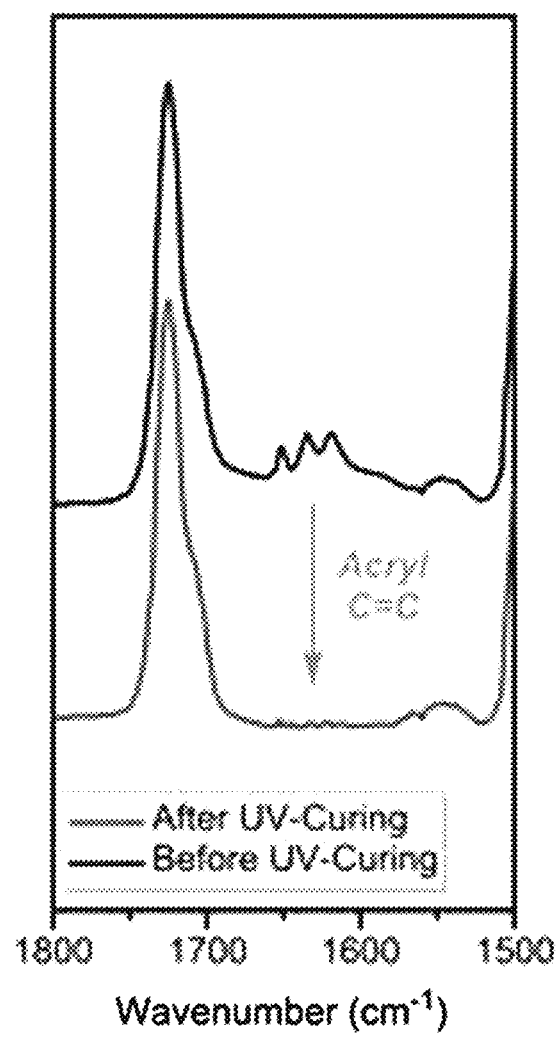
FIGS. 11A to 11C show FT-IR analysis results of hybrid films of Examples 12-14 before and after UV curing.
Figure 11B:
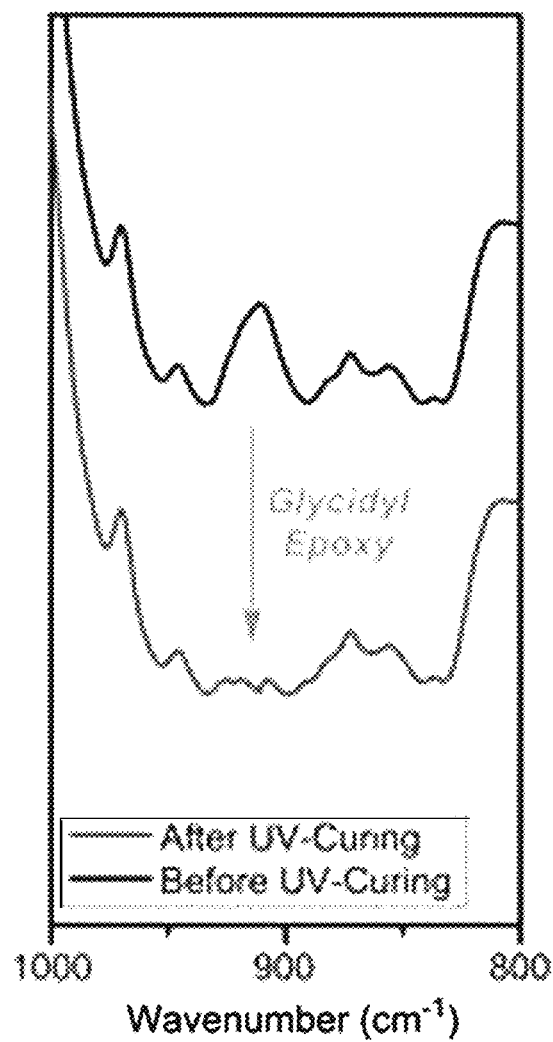
Figure 11C:
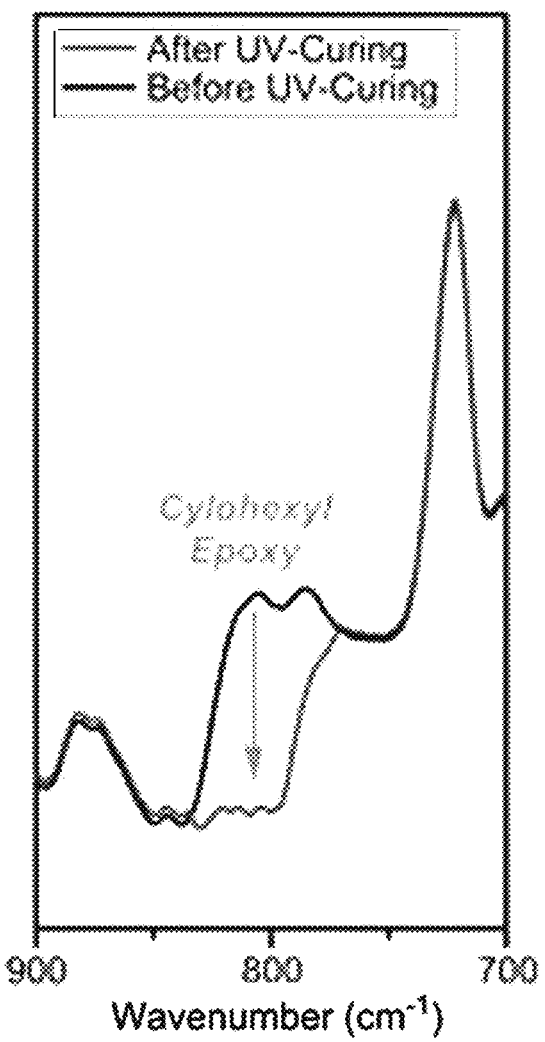

Referring to FIG. 9, it can be seen that the hybrid films of Examples 8-11 self-healed the scratches at 110° C. within 5 minutes via the retro-Diels-Alder reaction.

Figure 12A:
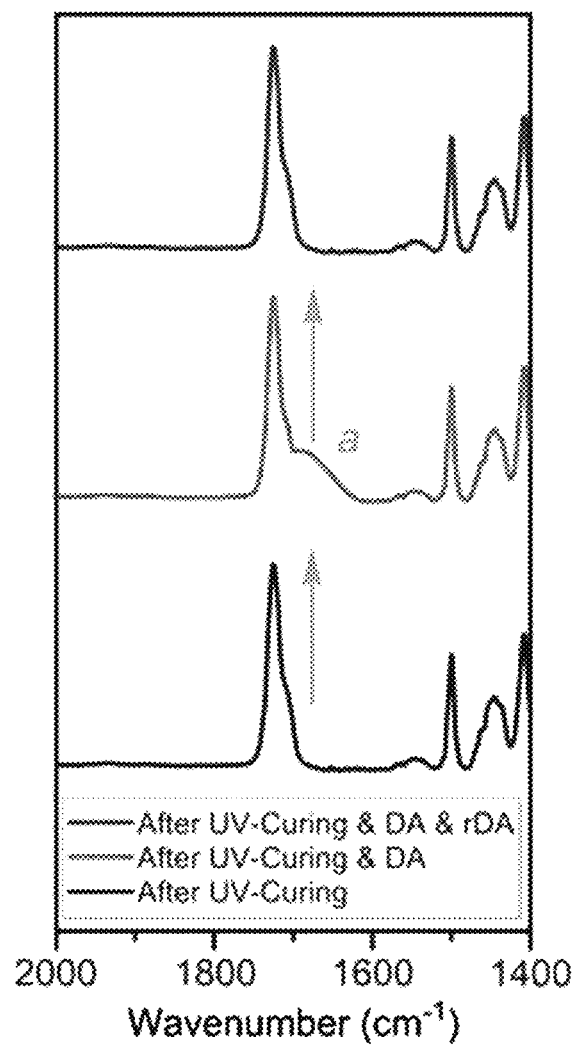
FIGS. 12A to 12C show FT-IR analysis results of hybrid films of hybrid films of Examples 12-14 after UV curing, after UV curing and DA crosslinking, and after UV curing and rDA crosslinking.
Figure 12B:
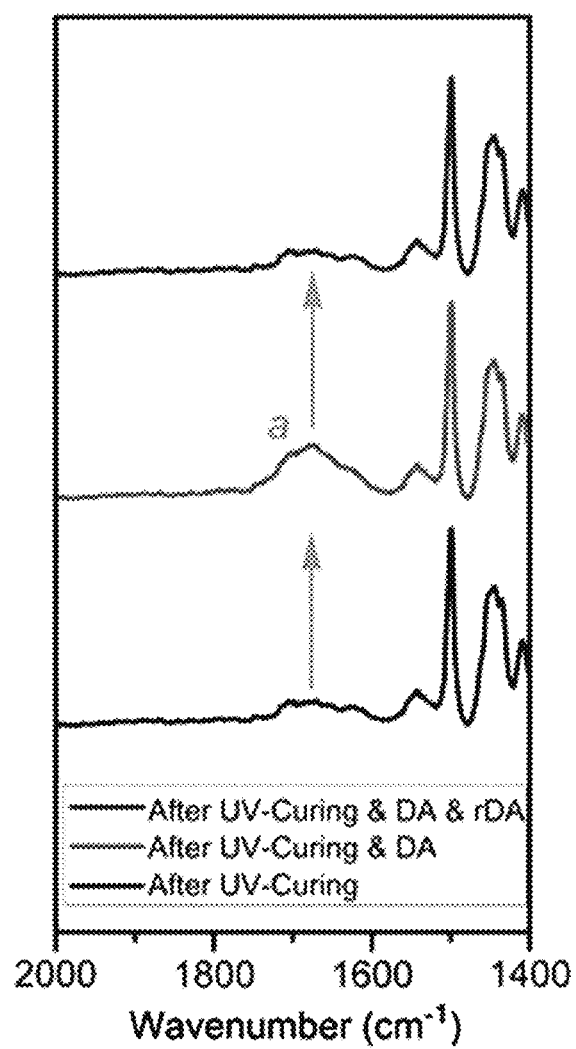
Figure 12C:
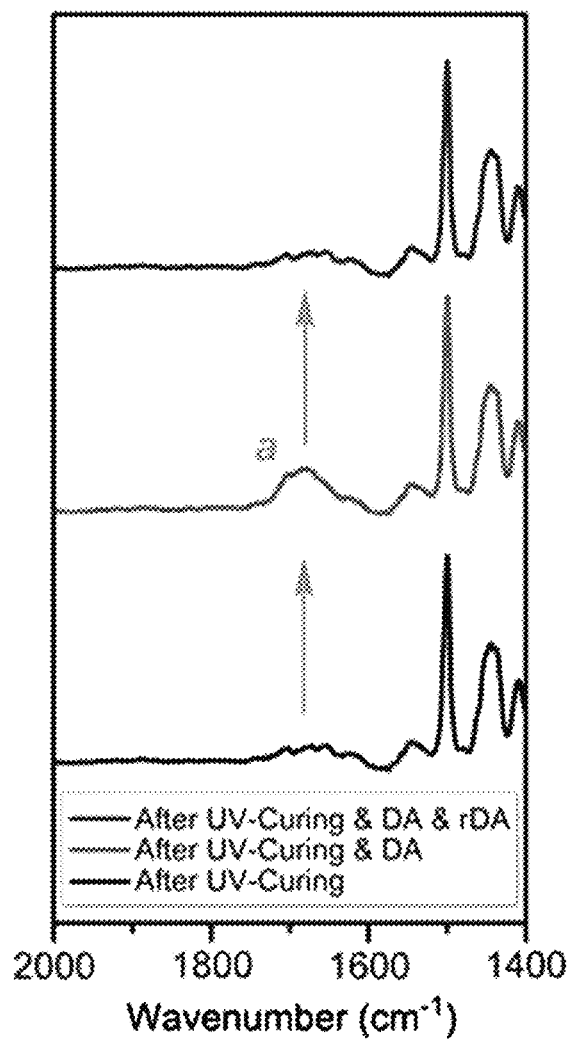
Figure 13A:
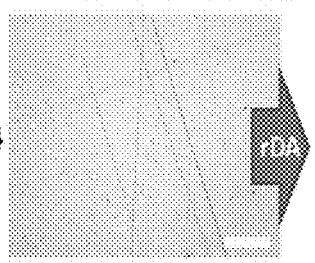
FIG. 13 show scratch test results of hybrid films of Examples 12-14 after UV curing and before FIGS. 13A to 13C and after FIGS. 13D to 13F thermally reversible self-healing.
Figure 13B:
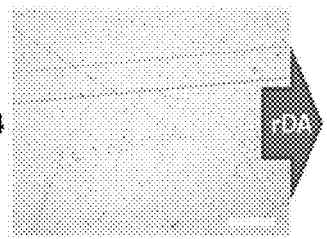
Figure 13C:
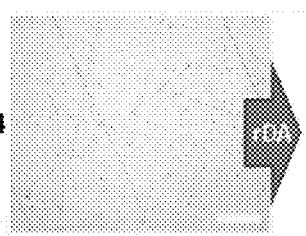
Figure 13D:
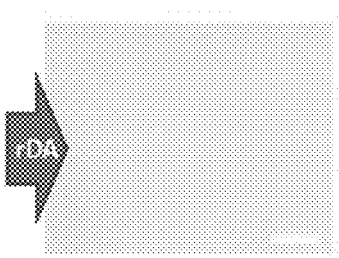
Figure 13E:
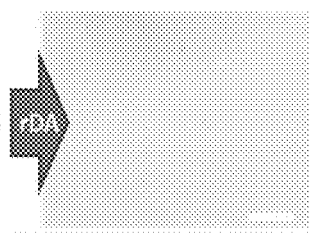
Figure 13F:
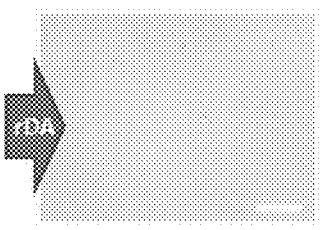
Figure 14A:
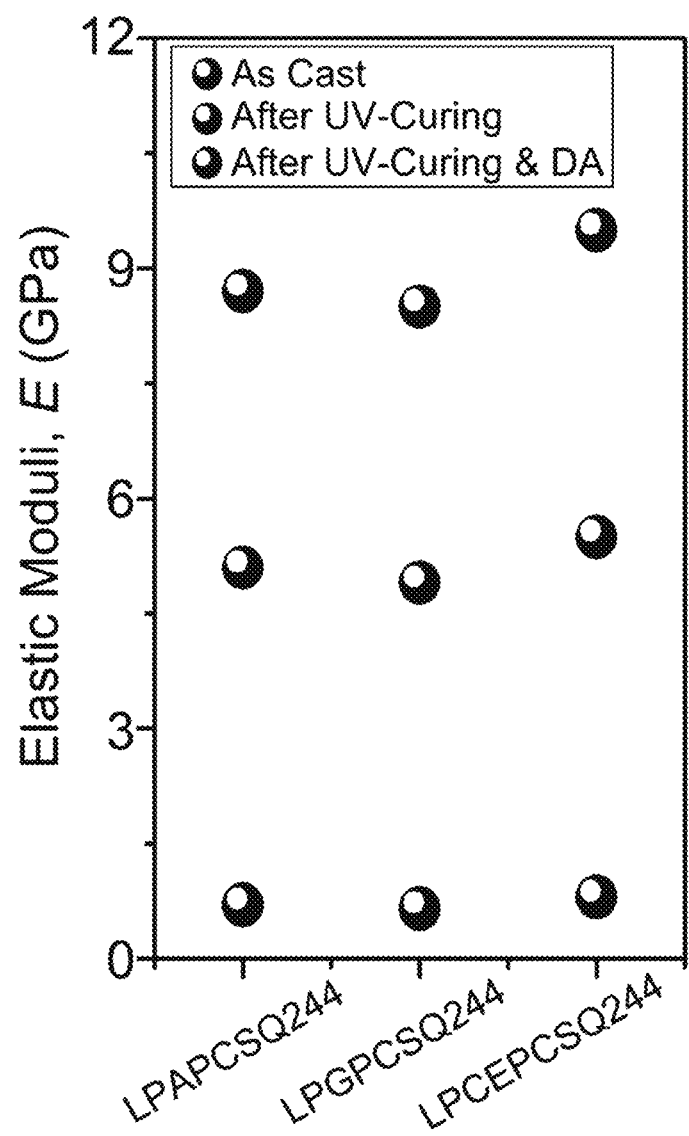
FIGS. 14A to 14C respectively show elastic moduli, surface hardness and brittleness indexes of hybrid films of Examples 12-14 before (as cast) and after UV curing and after thermally reversible self-healing (DA).
Figure 14B:
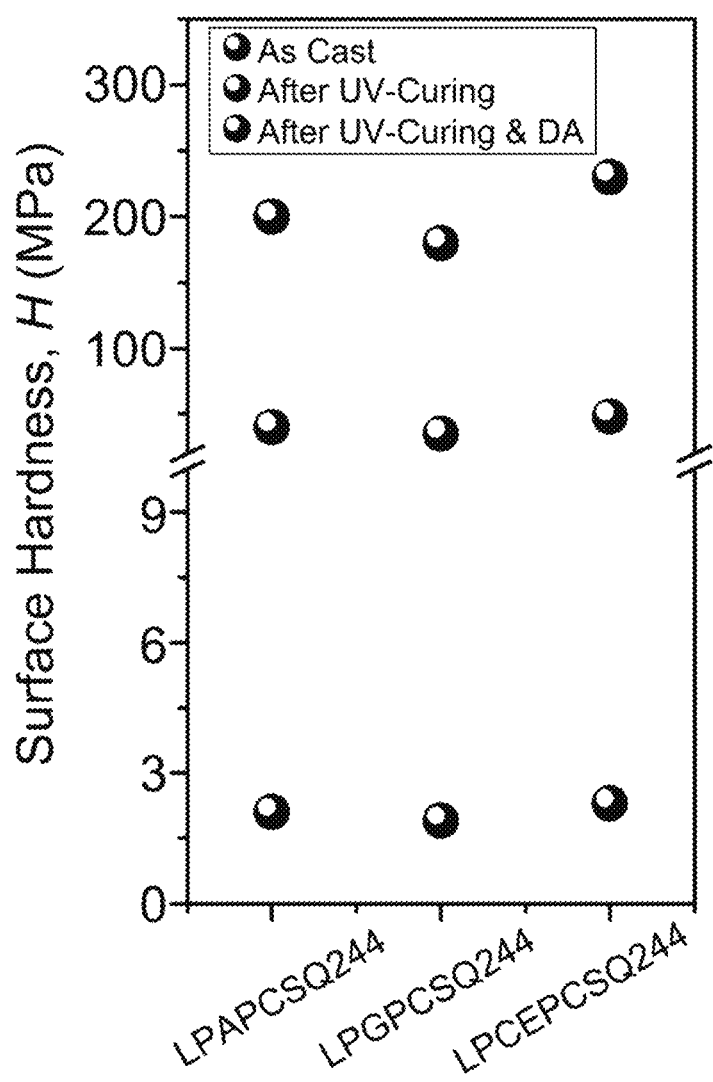
Figure 14C:
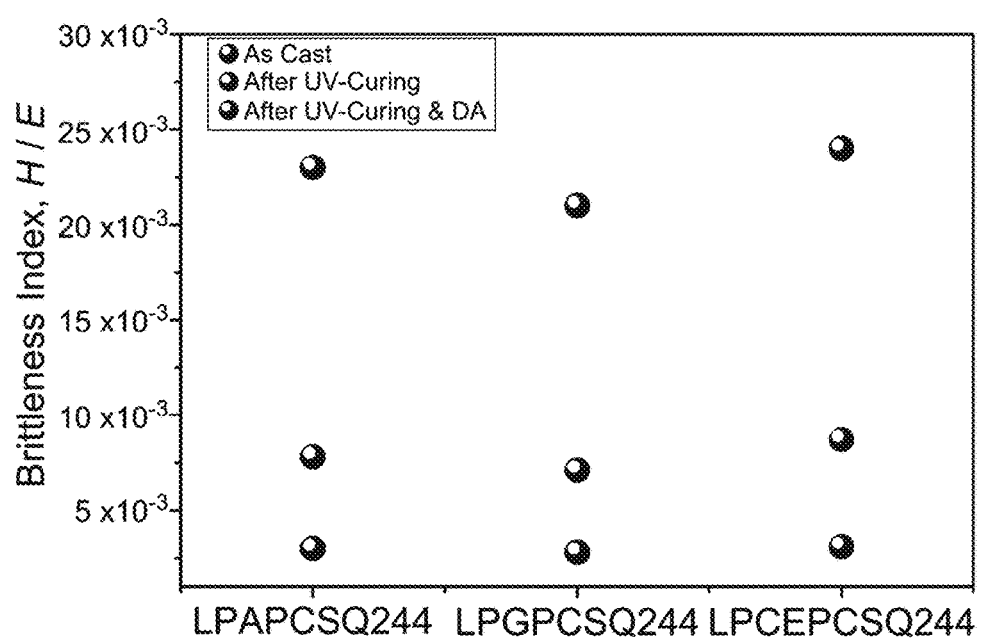

In addition, the hybrid films of Examples 12-14 were crosslinked by curing at 100° C. for 30 minutes via the DA (Diels-Alder) reaction. Then, after making scratches intentionally, they were heat-treated at 120° C. for 10 minutes such that the crosslinkage could be broken via the rDA (retro-Diels-Alder) reaction. The FT-IR analysis result is shown in FIGS. 12A to 12C. FIGS. 13A to 13F show the optical microscopic images showing that the scratches made after the DA crosslinking disappeared through self-healing.

According to the present disclosure, a polysilsesquioxane copolymer which can self-heal within several minutes at 100-120° C. after being crosslinked at 80-100° C. can be provided. The polysilsesquioxane copolymer, having a diene and a dienophile introduced together in the copolymer, can be used as a single material.

In addition, because the self-healing polysilsesquioxane copolymer significantly improves physical properties such as heat resistance, mechanical strength, light transmittance, solubility and processability when applied to a hybrid material such as a film, it is widely applicable as a coating material for displays or automobiles, in addition to gas separation membranes.

What is claimed is:

1. A self-healing polysilsesquioxane copolymer represented by Chemical Formula 1:

[Chemical Formula 1]

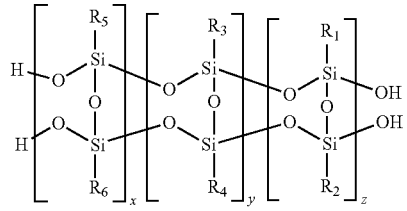

wherein each of $R_1$ through $R_6$, which are different from each other, is independently hydrogen or —$R_7$—$R_8$, $R_7$ is a valence bond or $C_1$-$C_6$ alkyl, $R_8$ is selected from a group consisting of a valence bond, $C_1$-$C_6$ alkyl, —$OR_9$, an organic functional group comprising a diene and an organic functional group comprising a dienophile, $R_9$ is selected from a group consisting of a hydrogen, $C_1$-$C_5$ alkyl, acryl, epoxy and epoxycyclohexyl, x is an integer from 1 to 10,000, y is an integer from 1 to 10,000, and z is an integer from 1 to 10,000, wherein the organic functional group containing the diene is represented by Chemical Formula 2 and the organic functional group containing the dienophile is represented by Chemical Formula 3:

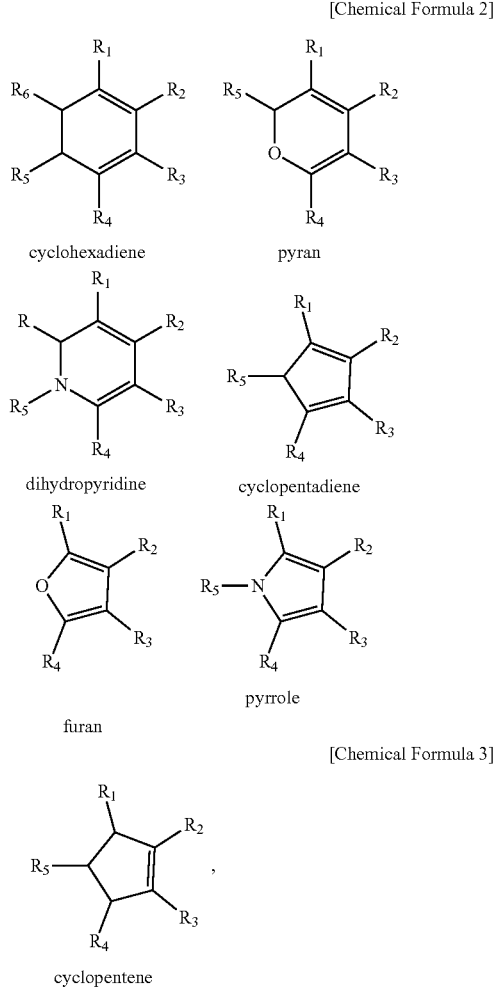

[Chemical Formula 2]

cyclohexadiene pyran dihydropyridine cyclopentadiene furan pyrrole

[Chemical Formula 3]

cyclopentene wherein each of $R_1$ through $R_5$ which are different from each other, is independently hydrogen, substituted or unsubstituted branched $C_1$-$C_{30}$ alkyl or $C_3$-$C_{10}$ cycloalkyl, wherein the substitution is with an amine or hydroxyl functional group and wherein the polysilsesquioxane copolymer contains at least one diene group and at least one dienophile group.

2. The self-healing polysilsesquioxane copolymer according to claim 1, wherein the polysilsesquioxane copolymer has a number-average molecular weight ($M_n$) of 100-100,000.

3. The self-healing polysilsesquioxane copolymer according to claim 1, wherein the polysilsesquioxane copolymer, after being crosslinked at 80-100° C., self-heals at 100-120° C. within several minutes.

4. A hybrid film comprising the polysilsesquioxane copolymer according to claim 1.

5. The hybrid film according to claim 4, wherein the hybrid film has a light transmittance of 80-100% at a wavelength of 500-800 nm.

6. The hybrid film according to claim 4, wherein the hybrid film has a thickness of 1 nm to 500 μm.

7. A gas separation membrane comprising the polysilsesquioxane copolymer according to claim 1.

8. A self-healing polysilsesquioxane copolymer represented by one of the following chemical formulas:

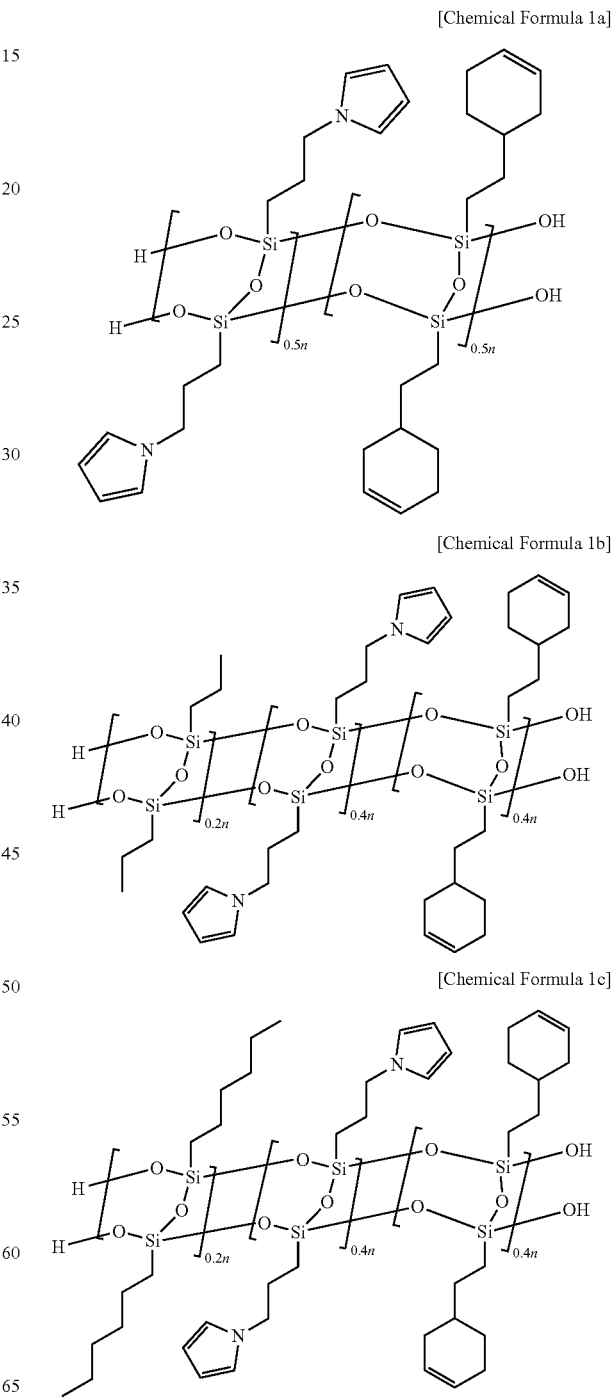

[Chemical Formula 1a]

[Chemical Formula 1b]

[Chemical Formula 1c]

[Chemical Formula 1d]

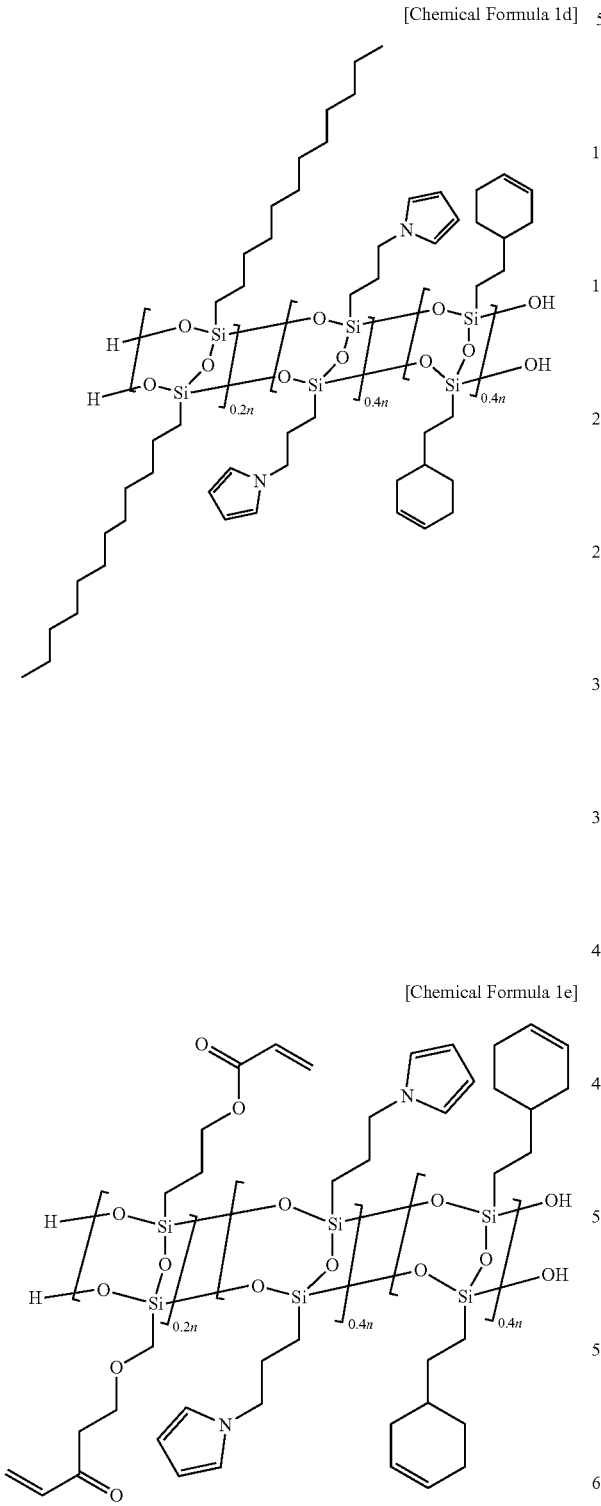

[Chemical Formula 1e]

[Chemical Formula 1f]

[Chemical Formula 1g]

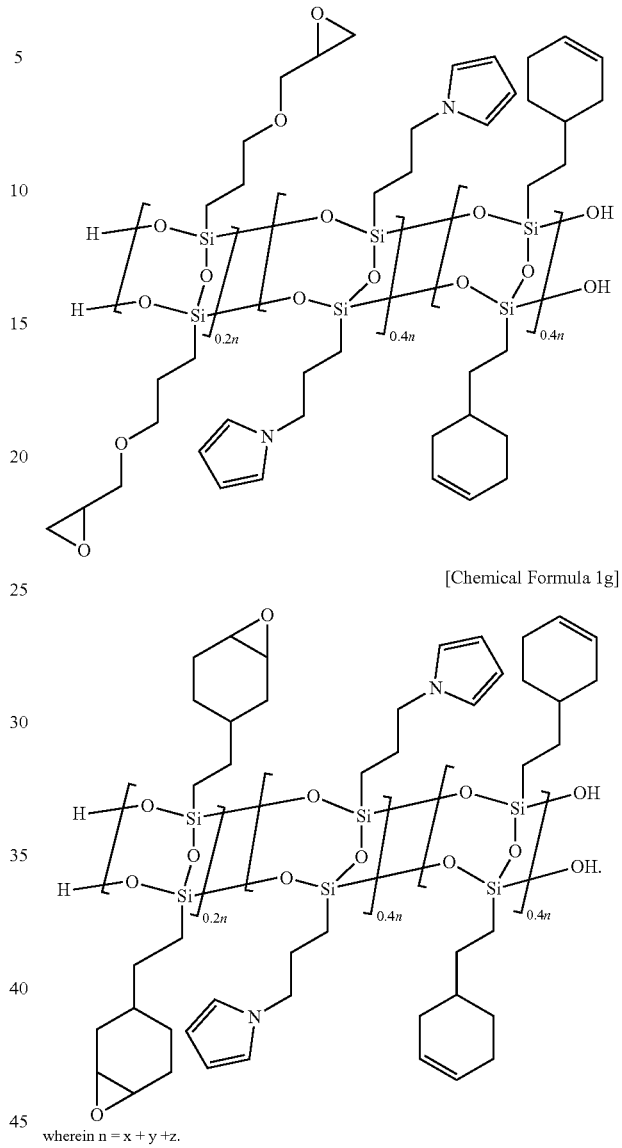

wherein n = x + y + z.

9. The self-healing polysilsesquioxane copolymer according to claim 8, wherein the polysilsesquioxane copolymer has a number-average molecular weight ($M_n$) of 100-100,000.

10. The self-healing polysilsesquioxane copolymer according to claim 8, wherein the polysilsesquioxane copolymer, after being crosslinked at 80-100° C., self-heals at 100-120° C. within several minutes.

11. A hybrid film comprising the polysilsesquioxane copolymer according to claim 8.

12. The hybrid film according to claim 11, wherein the hybrid film has a light transmittance of 80-100% at a wavelength of 500-800 nm.

13. The hybrid film according to claim 11, wherein the hybrid film has a thickness of 1 nm to 500 μm.

14. A gas separation membrane comprising the polysilsesquioxane copolymer according to claim 8.

* * * * *